US011783944B2

(12) United States Patent
Krouse

(10) Patent No.: US 11,783,944 B2
(45) Date of Patent: Oct. 10, 2023

(54) SYSTEM FOR LIVE MONITORING OF VITALS FOR PATIENTS AND PHYSICIANS

(71) Applicant: Neal F. Krouse, Boynton Beach, FL (US)

(72) Inventor: Neal F. Krouse, Boynton Beach, FL (US)

( * ) Notice: Subject to any disclaimer, the term of this patent is extended or adjusted under 35 U.S.C. 154(b) by 261 days.

(21) Appl. No.: 17/014,951

(22) Filed: Sep. 8, 2020

(65) Prior Publication Data
US 2021/0074422 A1    Mar. 11, 2021

Related U.S. Application Data

(60) Provisional application No. 62/897,884, filed on Sep. 9, 2019.

(51) Int. Cl.
*G16H 80/00* (2018.01)
*G16H 40/67* (2018.01)
*H04W 4/80* (2018.01)

(52) U.S. Cl.
CPC ............ *G16H 40/67* (2018.01); *G16H 80/00* (2018.01); *H04W 4/80* (2018.02)

(58) Field of Classification Search
CPC .......... G16H 40/67; G16H 80/00; H04W 4/80
USPC .......................................................... 705/2
See application file for complete search history.

(56) References Cited

U.S. PATENT DOCUMENTS

| | | | | |
|---|---|---|---|---|
| 6,402,691 B1* | 6/2002 | Peddicord | ............. | G16H 40/63 455/39 |
| 10,658,075 B1* | 5/2020 | Blackwell, Jr. | ........ | G16H 15/00 |
| 11,166,677 B2* | 11/2021 | Davis | .................... | A61B 5/1116 |
| 2005/0171444 A1* | 8/2005 | Ono | ..................... | A61B 5/0002 600/490 |
| 2006/0155589 A1* | 7/2006 | Lane | .................... | A61B 5/0002 705/4 |
| 2006/0238331 A1* | 10/2006 | Lee | ...................... | H04B 1/3805 340/539.1 |
| 2009/0018409 A1* | 1/2009 | Banet | ................... | A61B 5/0816 600/301 |
| 2009/0221884 A1* | 9/2009 | Ryan | ..................... | G16H 40/67 600/301 |
| 2011/0066010 A1* | 3/2011 | Moon | .................. | A61B 5/0205 600/509 |
| 2011/0137141 A1* | 6/2011 | Razoumov | .......... | A61B 5/0002 600/324 |
| 2011/0224498 A1* | 9/2011 | Banet | .................. | A61B 5/0002 600/300 |
| 2014/0200474 A1* | 7/2014 | Selvaraj | .............. | A61B 5/0806 600/529 |
| 2016/0098520 A1* | 4/2016 | Lulias | .................... | G16H 10/60 705/3 |
| 2017/0265782 A1* | 9/2017 | Vollmer | ................ | A61B 5/1112 |
| 2017/0319082 A1* | 11/2017 | Sayme | .................. | A61B 5/316 |
| 2020/0305793 A1* | 10/2020 | Al-Jadda | .............. | A61B 5/6823 |
| 2021/0043302 A1* | 2/2021 | Song | ........................ | G16H 40/67 |
| 2021/0361164 A1* | 11/2021 | Bogdan | ................. | A61B 5/308 |
| 2022/0068503 A1* | 3/2022 | Yuz | ......................... | G16H 80/00 |

(Continued)

*Primary Examiner* — Ankur Jain
(74) *Attorney, Agent, or Firm* — John C. Smith

(57) ABSTRACT

A smart phone app that provides an early warning platform for patients to transmit medical information to health care providers on a daily basis to help decrease the number of hospital readmissions by addressing problems before they become significant medical events.

15 Claims, 1 Drawing Sheet

(56) References Cited

U.S. PATENT DOCUMENTS

2022/0171839 A1\* 6/2022 Eidam ................... H04W 12/06
2022/0260589 A1\* 8/2022 Stubbe ............... G01N 33/6893

\* cited by examiner

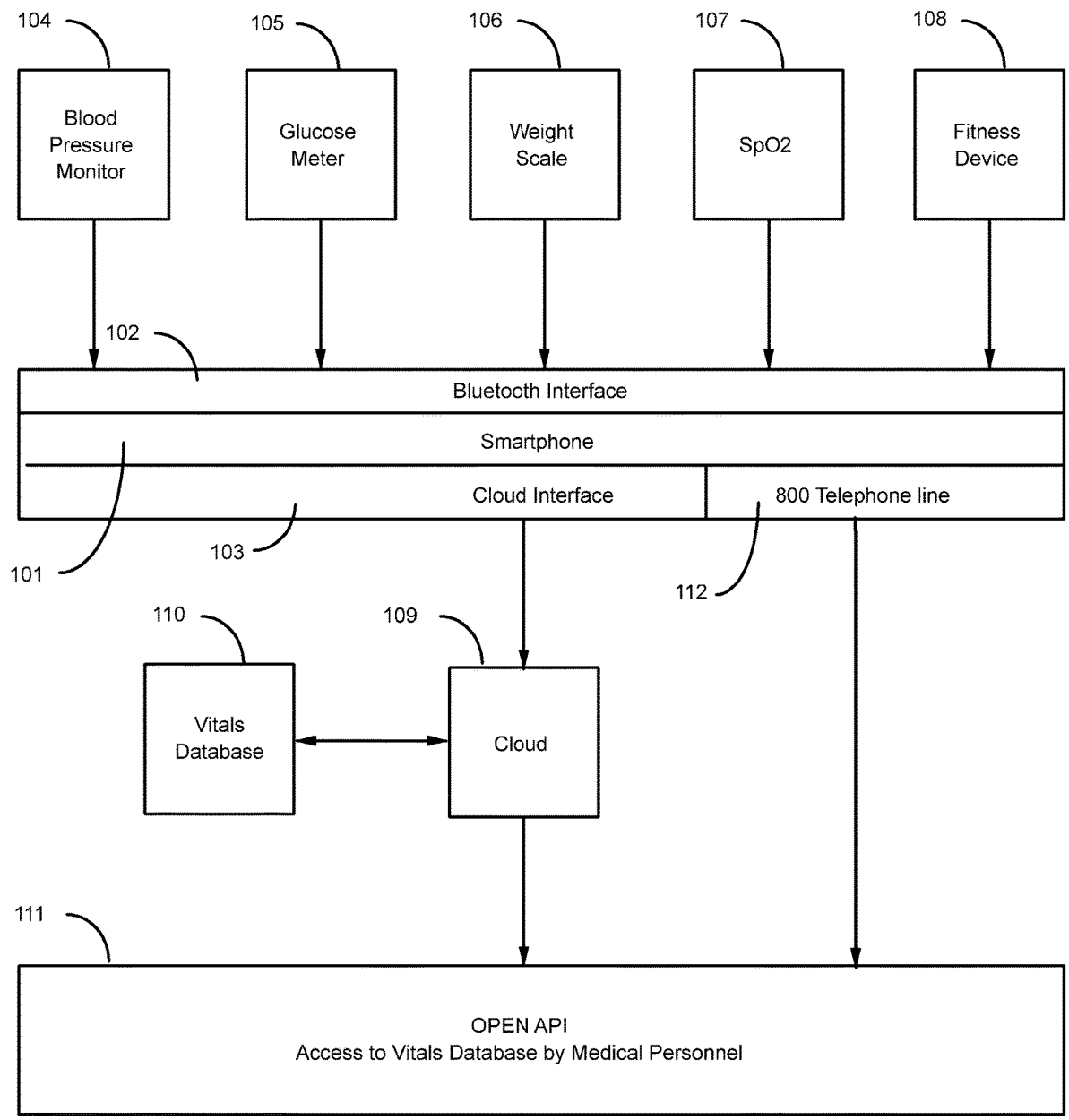

SYSTEM FOR LIVE MONITORING OF VITALS FOR PATIENTS AND PHYSICIANS

CROSS-REFERENCE TO RELATED APPLICATIONS

This application is related to, and claims the benefit of the provisional patent application entitled "System For Live Monitoring Of Vitals For Patients And Physicians", filed Sep. 9, 2019, bearing U.S. Ser. No. 62/897,884 and naming Neal F. Krouse, the named inventor herein, as sole inventor, the contents of which is specifically incorporated by reference herein in its entirety.

BACKGROUND OF THE INVENTION

Technical Field

The invention is related to medical monitoring systems. In particular, it relates to a method of improving preventative healthcare by automatically monitoring patient vitals without requiring office visits to a physician's or other healthcare provider's facility. It keeps track of patient vitals and, when an anomaly in the patient's vitals is detected, it automatically notifies the healthcare provider and transmits the vitals data to the healthcare provider.

Background

Today, many individuals have serious medical conditions that require ongoing monitoring of the patient's vitals by medical professionals for the purpose of detecting changes that may indicate a worsening of the patient's condition. However, the present day practice of having the patient go to a medical facility creates both a financial burden for the patient, as well as an inconvenience since the patient must expend time and effort to go to a medical facility for testing.

Another problem associated with prior art devices that measure vitals in a patient's home is that they have limited monitoring capabilities. They do not send out alerts for live monitoring support, even despite having Bluetooth-enabled devices.

The medical facilities are also burdened by their resources being consumed for what may be merely routine data collection. In addition, there is a burden placed on other providers, such as insurance companies, Medicaid, Medicare, etc.

While the prior art has provided numerous systems for monitoring patients in a hospital setting, it has failed to provide a preventative healthcare alternative that allows the patient to monitor day-to-day vitals without having to go to a medical facility. It would be desirable to provide patient's with preventative healthcare that reduces the financial and time burdens on the patient while simultaneously reducing the strain on medical facility resources, and in addition, providing savings on healthcare expenses.

SUMMARY OF THE INVENTION

The present invention provides Bluetooth-enabled vitals machines, located at a patient's residence, that communicate to physicians via application in real-time. Abnormal blood sugar, weight, blood pressure, pulse, blood oxygen levels, and other vitals can be detected and automatically initiate contact with health professionals so that they can immediately respond.

BRIEF DESCRIPTION OF THE DRAWINGS

FIG. 1 is a block diagram illustrating a preferred embodiment of the components of the live monitoring system.

DESCRIPTION OF THE PREFERRED EMBODIMENT

Prior to a detailed discussion of the FIGURES, a general overview of the invention will be presented.

Due to the high cost of medical care today, preventative healthcare is essential for personal and economy-level cost savings for healthcare expenses.

Preventative healthcare assists health providers, such as insurance companies, Medicare, Medicaid, and other health providers seeking to lower patient care costs and increase efficiencies.

Preventative healthcare also assists patients because it reduces the number of office visits. This reduces patient costs, and also reduces the inconvenience to the patient by doing preventive testing at home instead of the physician's office.

The invention uses a smart phone app that provides a platform for patients to transmit medical information to health care providers on a daily basis to help decrease the number of hospital readmissions by addressing problems before they become significant medical events.

For ease of discussion, the specification uses the term "smart phone app" when describing the invention. However, the term "smart phone" as used herein is used to describe a variety of devices. For example, the smart phone can in fact be a conventional "smart" cellular phone, but it can also be a tablet computer, a notebook computer, a personal computer, etc. The only requirement is that it be an intelligent device that can communicate with the monitoring devices in the patient's residence, and also communicate with systems used by medical professionals.

The invention provides Bluetooth-enabled vitals machines that communicate to physicians via a software application in real-time. Abnormal blood sugar, weight, blood pressure, pulse, or blood oxygen levels can be detected and responded to immediately. By using at-home measurements, the invention allows potential problems to be handled proactively without requiring an office visit.

The invention reduces the chances of patients experiencing dangerous medical conditions by monitoring patients in real time. In addition, it reduces the need for emergency room and urgent care visits while providing demonstrable savings in healthcare expenses.

An advantage of the invention is that it connects multiple Bluetooth-enabled devices to application software that in turn transmits a complete set of vitals data to the healthcare provider.

The preferred embodiment of the invention uses a smart phone app that provides a platform for patients to transmit medical information to medical professionals in real-time. The medical professionals include insurance providers, Medicare, Medicaid, physicians, as well as other authorized parties. The regular updates help to decrease the number of hospital readmissions by addressing problems as they occur, and before they become significant medical events.

The invention provides at-home human body monitoring that interfaces with health care providers to significantly reduce the chances of patients experiencing dangerous medical conditions in realtime. By monitoring patient vitals on a daily basis, the software application detects changes in the patient's condition before they become serious medical problems. In turn, this enables doctors to monitor patients on a daily basis to help decrease the number of hospital readmissions by addressing problems as they occur, and before they become serious medical events. Further, the invention addresses a need to reduce emergency room visits while providing simultaneously demonstrable savings in healthcare quality and expenses.

In the preferred embodiment, the invention uses Bluetooth enabled vitals machines that directly communicate with a smart phone application. The application receives essential vitals information from multiple monitoring devices and provides them to physicians and health professionals. No longer will delays occur that prevent the physician's review of important changes in patient vitals.

The invention provides several benefits. It saves money for Medicare, Medicaid and other insurance companies by reducing the chance of a patient having a significant medical event. It offers proactive care for the patient population. It also identifies patients who may be non-compliant in regularly monitoring their vitals at home per their self-care plan. By getting telephonic daily test results, the potential to reduce catastrophic events and readmission by about 20% for the non-compliant Medicare population and about 40% for the noncompliant Medicaid population.

The invention also increases worker productivity, allows employees and individuals to address medical problems without leaving work or home, and maximizes access to physician care so patients can seek treatment for medical issues quickly and proactively. It reduces the need for high-priced doctor's office and emergency room visits while providing demonstrable savings in healthcare expenses.

The invention enables end users to increase exposure to physician monitoring. Patients take their vitals using provided Bluetooth-enabled machines. The vitals data is then sent in real time from a patient's own in-home clinical devices via the smart phone app. Physicians receive vitals information, such as blood pressure, glucose levels, weight, heart rate, cot, oxygen saturation, BMI and more. The foregoing list of monitoring devices is for ease of illustration.

By way of example, the preferred in embodiment envisions a system that may include:
1) A scale.
2) A blood pressure cuff.
3) An O2 saturation monitor.
4) A glucometer.

Those skilled in the art will recognize that the foregoing list of monitoring devices is not limited and can include any number of medical devices can be incorporated into the system based on the patient's individual needs In the preferred embodiment, the devices are provided to the patient via insurance, Medicaid, Medicare, or another healthcare provider. The devices relay findings to a smart phone app which in turn transmits them to the physician's medical records database. In addition to simply capturing the data, the system contributes to the significance of this real-time monitoring system. For example, physicians will receive an alert if the patient's vitals are above or below physician-set trigger thresholds. For instance, if a blood sugar reading is above 200, or if the pulse rate is irregular or above 100, or if the blood pressure systolic is above 180 or diastolic above 100, then the physician will be delivered an urgent notice.

Another advantage of the invention is that it allows the physician to determine if and where the alert should be sent in addition to medical record storage. The alert can be sent to an office land line, the physician's tablet, the physician's smart phone, a healthcare facility that the physician is associated with, etc. Data transmitted can include:
1) Pulse Ox (Oxygen Saturation)
2) Heart Rate/Pulse
3) Blood Pressure
4) Glucometer Measurements
5) Weight/BMI
6) Temperature In addition to transmitting real time essential vital signs to the patient's primary care physicians, EMR, and/or any other appropriate entity. The data transmitted by the system preferably includes the doctors' names, patient name and type of alert. Real time reporting is a valuable aid for preventing or minimizing larger patient health problems that may occur due to time delays in prior art treatment programs. For instance, a sudden weight gain could be a sign of possible congestive heart failure. Likewise, a low oxygen saturation (below 90) could signal pneumonia, asthma, or worsening of COPD.

The early warning system provided by the invention keeps people allows treatment in the early stages of a medical problem, and helps reduce emergency room visits and reduces hospital readmissions. This results in a significantly cost-effective benefit because of the real-time transmissions of vital signs using wireless technology. The platform's data collection and real-time notifications enables a more complex understanding of patients' health and habits to accelerate strategic healthcare. From patient engagement to care coordination and wellness programs, the platform connects healthcare providers and patients to improve health, mitigate risks, streamline costs, and manage health more effectively.

Alerts and vitals data are delivered instantly to monitoring providers via a variety of data paths. For example, information can be reviewed via:
1) Tablet & Mobile App
2) Online Dashboard
3) Patient Medical Records The benefits provided by the invention improves patient health and significantly reduces healthcare costs. It provides a unique smart phone based platform for patients to transmit medical information to primary care doctors on a daily basis to help decrease the number of emergency room and hospital readmissions. Some of the health concerns that are monitored include, but are not limited to, are:
1) Daily vital signs
2) Lab results
3) Irregular heart rhythm
4) ACF
5) Atrial fibrillations
6) CVA
7) TIA
8) Uncontrolled hypertension
9) Hyperglycemia Having discussed the features and advantages of the invention in general, we turn now to a more detailed discussion of the FIGURES.

FIG. 1 is a block diagram illustrating a preferred embodiment of the components of the live monitoring system.

In the preferred embodiment, a smart phone 101 provides the platform used to accumulate the vitals data and transit it to health professionals. The smart phone can be any suitable smart phone device. The only additional feature required is the software application the drives the system.

The smart phone uses Bluetooth communications 102 to communicate with the vitals monitoring devices 104-108. The devices 104-108 shown in this FIGURE are provided as examples of the type of monitoring devices that the invention can use. Those skilled in the art will realize that any type of monitoring device, currently existing or developed in the future, can be incorporated into the system so long as it has suitable Bluetooth communications capability. For example, if non-invasive glucose monitoring devices are successfully developed in the future, and used individually or incorporated into fitness monitoring bracelets or watches, they can be used to input data to the smart phone 101. Likewise, currently available fitness bracelets that are currently available in commerce for measuring physical activity such as steps, distance, swimming, sleep, calories burned, etc., can be modified such that the data created by that type of device can be transmitted by the smart phone software to medical professionals.

Those skilled in the art will realize that medical technology is constantly evolving, and many new monitoring devices will be developed over time. A significant advantage provided by the invention is that the smart phone software can be easily modified as new devices becomes available, and as a result, medical professionals will be provided with even more robust data as time goes on.

Also shown in the smart phone 101 is a cloud interface 103 that allows vitals data to be transferred to a vitals database 110 via the cloud 109. In addition to transferring data via the cloud 109, the invention provides an alternative method of transferring data to medical professionals by using a conventional telephone link that optionally uses an 800 number. Of course, a standard dial connection using a non-800 telephone link can also be used.

Once the vitals data is available in the vitals database 110, it can then be accessed by healthcare professionals via the open API function 111, or accessed by healthcare professionals in response to alerts transmitted from the smart phone 101.

While the invention has been described with respect to a preferred embodiment thereof, it will be understood by those skilled in the art that various changes in detail may be made therein without departing from the spirit, scope, and teaching of the invention. For example, the number and type of monitoring devices can vary, the cloud function can be replaced by any suitable technology, etc. Accordingly, the invention herein disclosed is to be limited only as specified in the following claims.

What is claimed is:

1. A healthcare monitoring system for automatically monitoring patient vitals without requiring visits to a physician or other healthcare provider's facility, comprising:
   a plurality of vitals monitoring devices, outside of a physician or other healthcare provider's facility, and at the patient's residence or other selected location, each having a wireless communications interface;
   a smart phone having a vitals data aggregation application, further comprising:
      a wireless communications interface for communicating with the wireless communications interfaces in the plurality of vitals monitoring devices; and
      an interface for communicating with an external computer system;
   a vitals database for storing vitals data transmitted by the vitals data aggregation application;
   an open API, for accessing vitals data in the vitals database; and
   the vitals data aggregation application provides access to the vitals data by healthcare professionals, and when an anomaly in the vitals is detected, it automatically transmits the vitals data to selected healthcare professionals;
   whereby the patient can monitor vitals data at home or outside of a healthcare facility without going to a healthcare facility, and automatically contact the healthcare facility when an anomaly in the vitals data is detected.

2. A healthcare monitoring system, as in claim 1, wherein:
   at least one of the plurality of vitals monitoring devices is a blood glucose meter that further comprises a wireless communications interface to transfer glucose measurements to the smart phone; and
   the vitals data aggregation application stores the glucose measurement in the vitals database when the glucose data is received by the smart phone.

3. A healthcare monitoring system, as in claim 1, wherein:
   at least one of the plurality of vitals monitoring devices is a blood pressure monitor that further comprises a wireless communications interface to transfer glucose measurements to the smart phone; and
   the vitals data aggregation application stores the blood pressure measurements in the vitals database wherein the blood pressure data is received by the smart phone.

4. A healthcare monitoring system, as in claim 1, wherein:
   at least one of the plurality of vitals monitoring devices is a weight scale that further comprises a wireless communications interface to transfer weight measurements to the smart phone; and
   the vitals data aggregation application stores the weight measurements in the vitals database when the weight measurement data is received by the smart phone.

5. A healthcare monitoring system, as in claim 1, wherein:
   at least one of the plurality of vitals monitoring devices is an oxygen saturation measurement device that further comprises a wireless communications interface to transfer oxygen saturation measurements to the smart phone; and
   the vitals data aggregation application stores the oxygen saturation measurements in the vitals database when the oxygen saturation data is received by the smart phone.

6. A healthcare monitoring system, as in claim 1, wherein:
   at least one of the plurality of vitals monitoring devices is a fitness measurement device that further comprises a wireless communications interface to transfer fitness measurements to the smart phone; and
   the vitals data aggregation application stores the fitness measurements in the vitals database when the fitness data is received by the smart phone.

7. A healthcare monitoring system, as in claim 6, wherein:
   the fitness measurement device is a smart wristwatch.

8. A healthcare monitoring system, as in claim 1, wherein:
   the smart phone has a cloud communications interface to communicate with an external computer that is associated with health care professionals.

9. A healthcare monitoring system, as in claim 8, wherein:
   the smart phone automatically communicates the vital data to the external computer associated with health care professionals when measured vital data indicates potential health problem, at predetermined times, when initiated by the user of the smart phone, or when initiated by the external computer that is associated with health care professionals.

10. A healthcare monitoring system, as in claim 9, wherein:

the health care processionals that access vital data are physicians, nurses, insurance providers, Medicare, Medicaid, and authorized parties.

11. A healthcare monitoring system, as in claim 10, wherein
the healthcare monitoring system automatically transmits vitals data to the physician when measured vital data exceeds predetermined limits set by the physician.

12. A healthcare monitoring system, as in claim 1, wherein:
the smart phone has a telephone communications interface to communicate with an external computer that is associated with health care professionals.

13. A healthcare monitoring system, as in claim 12, wherein:
the smart phone automatically communicates the vital data to the external computer associated with health care professionals when measured vital data indicates potential health problem, at predetermined times, when initiated by the user of the smart phone, or when initiated by the external computer that is associated with health care processionals.

14. A healthcare monitoring system, as in claim 13, wherein:
the health care professionals that access vital data are physicians, nurses, insurance providers, Medicare, Medicaid, and authorized parties.

15. A healthcare monitoring system, as in claim 14, wherein:
the healthcare monitoring system automatically transmits vitals data to the physician when measured vital data exceeds predetermined limits set by the physician.

\* \* \* \* \*